United States Patent
Loubens et al.

(10) Patent No.: US 6,547,805 B1
(45) Date of Patent: Apr. 15, 2003

(54) SURGICAL INSTRUMENT AND CONNECTOR FOR PERMITTING INDEPENDENT ASSEMBLY AND DISASSEMBLY OF A MOBILE CUTTING ELEMENT AND A MOBILE GRIP FROM A FIXED BODY OF THE INSTRUMENT

(75) Inventors: Thierry Loubens, Lyons (FR); Lionel Riou, Lyons (FR); Christophe Garin, Lyons (FR)

(73) Assignee: Soprane SA, Lyons (FR)

( * ) Notice: Subject to any disclaimer, the term of this patent is extended or adjusted under 35 U.S.C. 154(b) by 0 days.

(21) Appl. No.: 09/720,739
(22) PCT Filed: Jun. 25, 1999
(86) PCT No.: PCT/JP99/03407
§ 371 (c)(1),
(2), (4) Date: Feb. 16, 2001
(87) PCT Pub. No.: WO00/01312
PCT Pub. Date: Jan. 13, 2000

(30) Foreign Application Priority Data

Jul. 3, 1998 (FR) .............................. 98 08706

(51) Int. Cl.⁷ .......................... A61B 17/28; A61B 17/32
(52) U.S. Cl. ........................................ 606/206; 606/171
(58) Field of Search ................................. 606/170, 171, 606/206, 205, 207, 208, 167

(56) References Cited

U.S. PATENT DOCUMENTS 6,126,674 A * 10/2000 Janzen ........................ 606/206

FOREIGN PATENT DOCUMENTS

| DE | 29601208 | 3/1996 |
| DE | 29708568 | 8/1997 |
| DE | 29718969 | 3/1998 |
| EP | 0706780 | 4/1996 |

* cited by examiner

Primary Examiner—Peter Nerbun
(74) Attorney, Agent, or Firm—Dowell & Dowell, P.C.

(57) ABSTRACT

A connecting device for a surgical instrument having at least one mobile cutting element which is reciprocally movable relative to a fixed jaw by operation of a resiliently loaded mobile grip wherein the connecting device includes an indexing mechanism which can be moved to a first position to permit mounting or removal of the mobile cutting element and a second position to permit independent mounting or removal of the mobile grip.

20 Claims, 15 Drawing Sheets

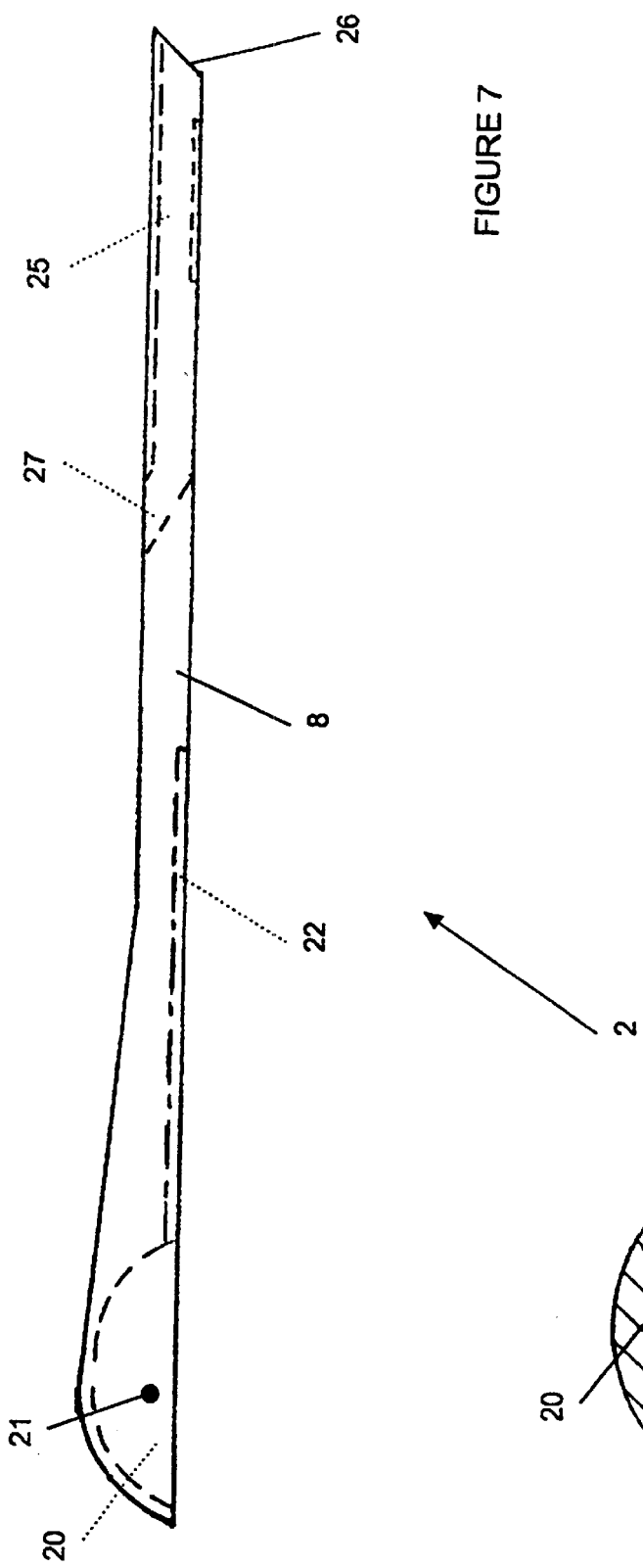
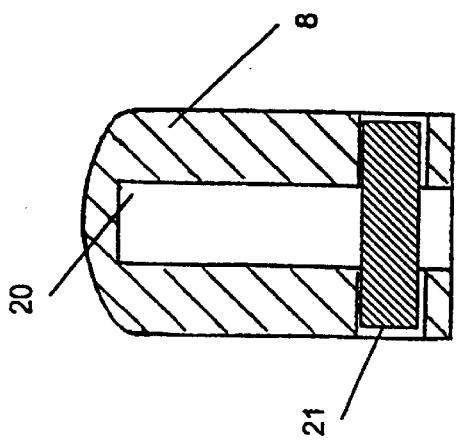

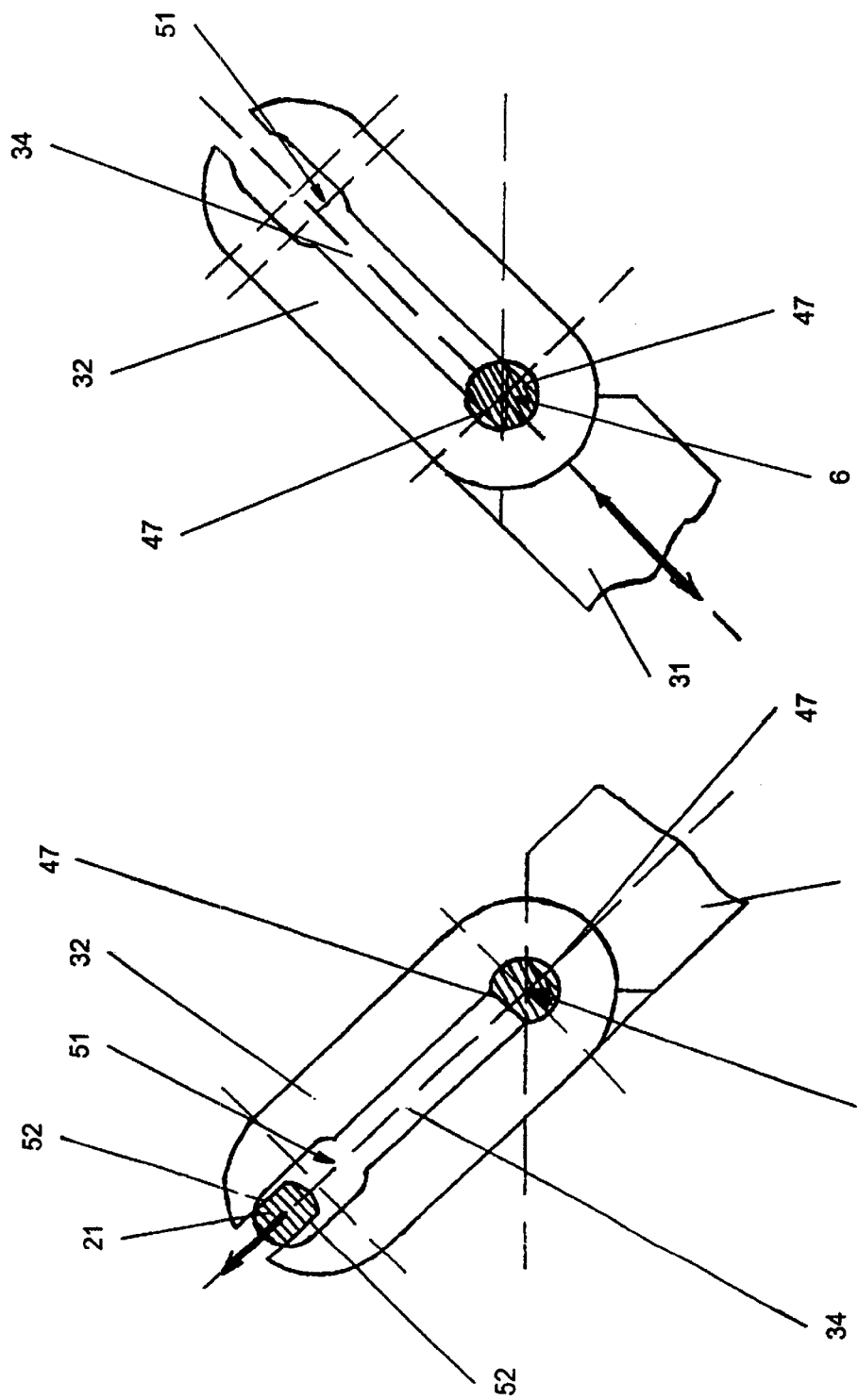

SURGICAL INSTRUMENT AND CONNECTOR FOR PERMITTING INDEPENDENT ASSEMBLY AND DISASSEMBLY OF A MOBILE CUTTING ELEMENT AND A MOBILE GRIP FROM A FIXED BODY OF THE INSTRUMENT

BACKGROUND OF THE INVENTION

1. Field of the Invention

The present invention relates to a surgical instrument comprising a connecting device which permits, according to defined and independent positions, the rapid assembly and/or dismantling of the mobile cutting element and its actuating grip.

The connecting device is intended for surgical instruments comprising cutting elements which slide relative to one another.

The connecting device is more particularly applicable to surgical instruments comprising a fixed cutting element and a mobile cutting element which are actuated by the agency of an elastically loaded mobile grip.

2. Description of the Related Art

The applicant has filed patent applications FR 98/05 689 and FR 98/05 690 in France relating to a surgical instrument and a connecting device.

The surgical instrument possesses a main body on which a mobile clamping jaw slides by the agency of an elastically loaded grip.

The main body is formed by a fixed grip which is extended by an elongate support forming a fixed clamping jaw. The mobile clamping jaw, which is actuated by means of the elastically loaded grip, slides on the fixed clamping jaw in a longitudinal direction.

The fixed and mobile clamping jaws respectively possess, opposite the fixed and mobile grips, cutting means which interact with each other during the longitudinal displacements of the said mobile clamping jaw to make successive cuts in the hard bone tissue or soft tissue of a patient.

The connecting device in patent applications FR 98/05 689 and FR 98/05 690 merely permit the rapid assembly and dismantling of the mobile element without parts of the, instrument having to be withdrawn. The connecting device comprises means for the angular indexing of the,mobile grip about its axis of rotation to permit, in a given position, the positioning or withdrawal of the mobile element of the main body of the instrument.

SUMMARY OF THE INVENTION

The purpose of the connecting device according to the present invention is to improve that described in patent applications FR 98/05 689 and FR 98/05 690 in the name of the applicant so as to enable, in predefined and independent positions, both the assembly or dismantling of the mobile element and the assembly or dismantling of the mobile grip.

The connecting device for a surgical instrument according to the present invention comprises indexing means defining a first series of angular positions permitting the positioning or withdrawal of the mobile element and a second series of angular positions, independent of the first, for the assembly or dismantling of the mobile grip.

The connecting device according to the present invention possesses angular indexing means which are formed by:

an elastically loaded pivot for the pivoting of the mobile grip relative to the fixed grip of the main body of the instrument, and guide means solidly fixed to the said mobile grip and interacting with the said pivot and a drive spindle provided on the mobile element for its longitudinal movements relative to the main body.

BRIEF DESCRIPTION OF DRAWINGS

The description which follows, having regard to the attached drawings, which are given by way of non-limiting examples, will provide a better understanding of the invention, the features which it possesses and the advantages which it is capable of providing:

FIGS. 7 to 14 are views showing, in detail, the mobile element sliding on the main body of the surgical instrument.

FIGS. 21a and 22a are views showing the extreme positions of the mobile grip on the main body for the positioning or withdrawal of the mobile cutting element when the pivot is in the position according to FIG. 20.

FIGS. 21e and 22e are views showing the extreme positions of the mobile grip on the main body during its positioning or withdrawal when the pivot is in the position according to FIG. 20

DESCRIPTION OF THE PREFERRED EMBODIMENT

Figure 1:
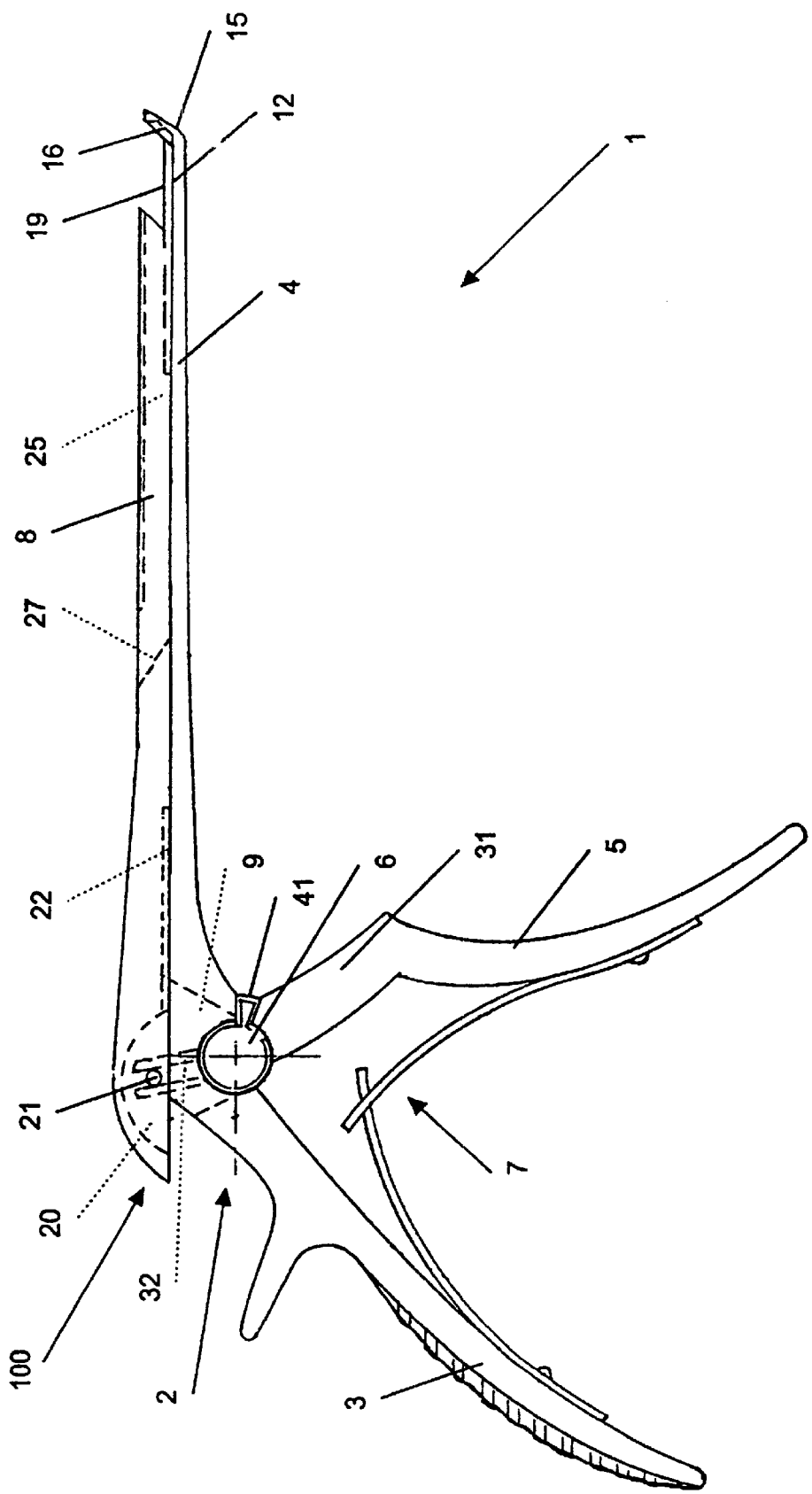
FIG. 1 is a view showing a surgical instrument according to the present invention.
Figure 2:
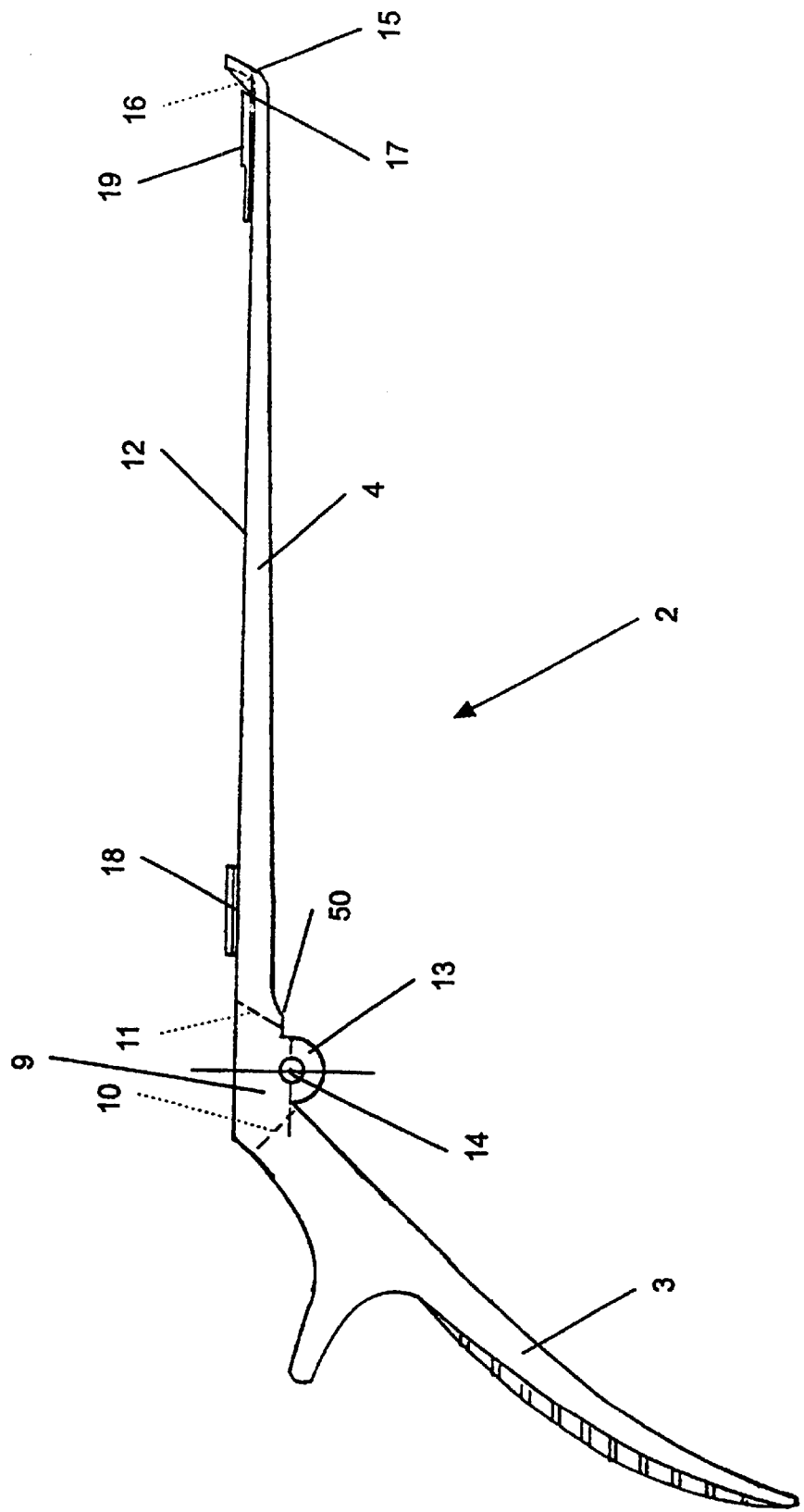
FIGS. 2 to 6 are views show the main body of the surgical instrument in detail.

FIG. 1 shows a surgical instrument 1 of the Kerrison forceps type, comprising a connecting device 100 which permits, in accordance with defined and independent angular positions, the rapid assembly and/or dismantling of a mobile cutting element 8 and of its actuating grip 5.

The surgical instrument 1 comprises a main body 2 formed by a fixed grip 3 which is extended in a substantially horizontal plane by a fixed element or an elongate support 4 constituting a fixed clamping jaw.

The main body 2 comprises, at the junction between the fixed grip 3 and the fixed clamping jaw 4, a mobile grip 5 which pivots about an elastically loaded pivot 6.

The mobile grip 5 is connected to the fixed grip 3 by spring plates 7 which are provided between the two grips to restore the mobile grip 5 to its original position after each pivoting movement.

The fixed clamping jaw 4 of the main body 2 interacts with a mobile element or a mobile clamping jaw 8 which slides in a longitudinal direction from front to rear on the said fixed clamping jaw 4 when a force is applied to the mobile grip 5.

The connecting device 100 comprises angular indexing means which make it possible to set the mobile grip 5 in defined and independent angular positions for the positioning or withdrawal of the mobile element 8 of the main body 2, on the one hand, and the assembly or dismantling of the mobile grip 5 of the said body, on the other hand.

FIGS. 2 to 6 show the main body 2 which possesses, within its thickness and at the point of the junction between the grip 3 and the clamping jaw 4, an aperture of conical profile 9 delimited by opposite and inclined surfaces 10, 11 in order that the more open side of the said aperture faces towards the upper edge 12 of the fixed clamping jaw 4.

The main body 2 comprises, on each side of the aperture 9, an arcuate lug 13 which is pierced by a drilled hole 14 intended to receive the pivot 6 to guide the mobile grip 5 in rotation.

The maximum travel of the mobile grip 5 about the pivot 6 within the aperture 9 of the main body 2 is delimited by the inclined and opposite surfaces 10, 11, as will be more clearly seen in due course.

The fixed clamping jaw 4 possesses, towards its free end which is opposite to the end through which the aperture 9 passes, a tip 15 extending in a substantially vertical direction, either upwards or downwards relative to the longitudinal axis of the surgical instrument 1.

Figure 5:
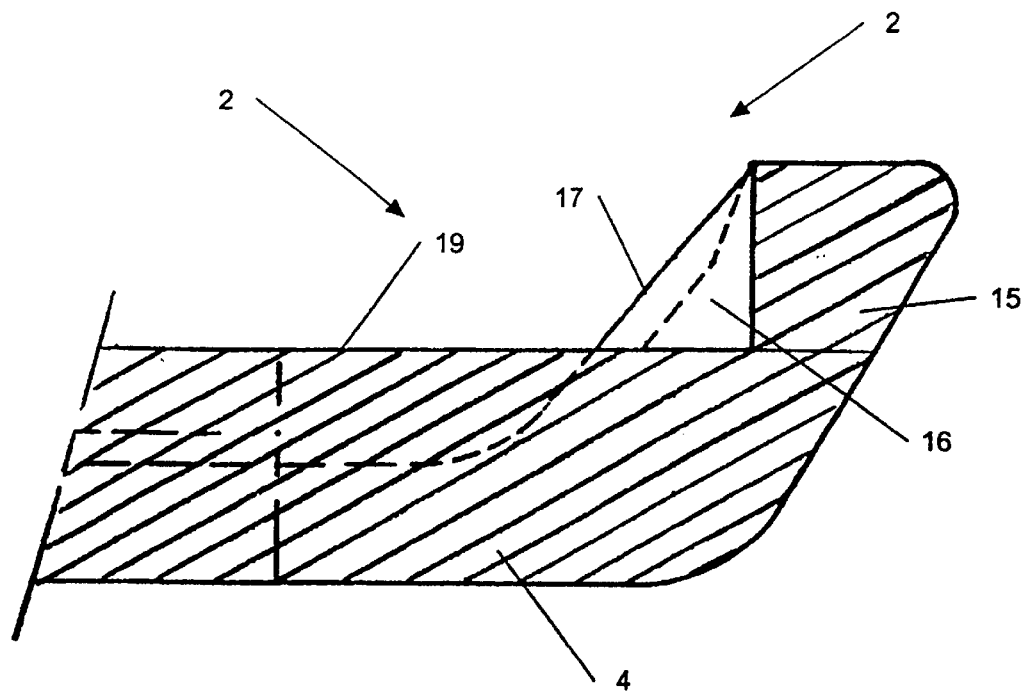

The tip 15 possesses, within its thickness, a hollow 16 delimiting opposite edges 17 which are inclined relative to the upper edge 12 of the fixed clamping jaw 4. The edges 17 of the tip 15 are machined to form cutting elements in order to cut bony fragments or soft tissue (FIG. 5).

Figure 6:
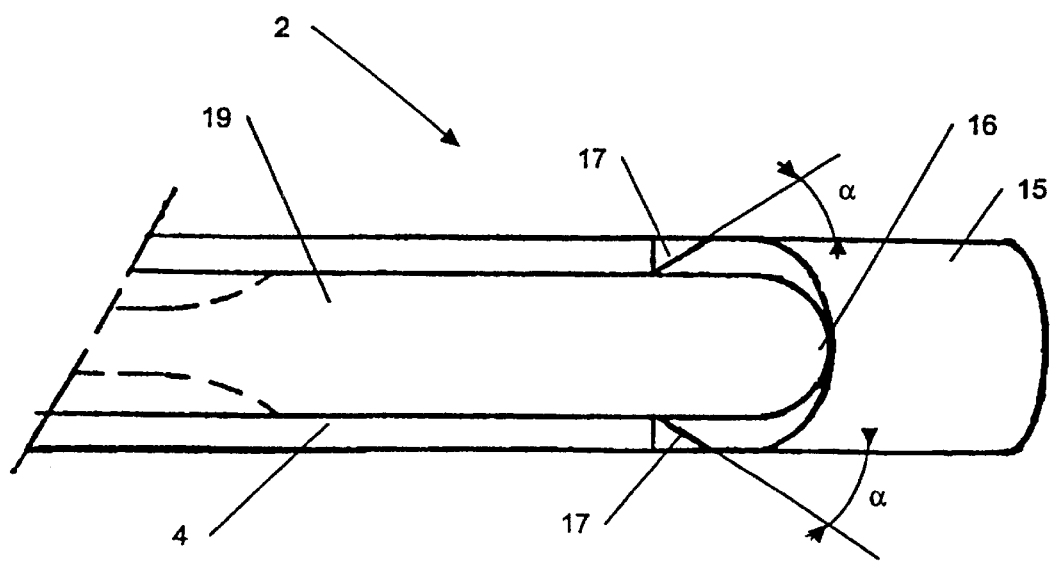

The opposite edges 17 of the tip 15 are chamfered outwards at an angle $\alpha$ of approximately 30 degrees relative to the outer edge of the said tip (FIG. 6).

The fixed clamping jaw 4 is solidly fixed, at its upper edge 12 and opposite the tip 15, to a T-shaped peg 18 allowing the longitudinal guiding of the mobile clamping jaw 8.

Figure 3:
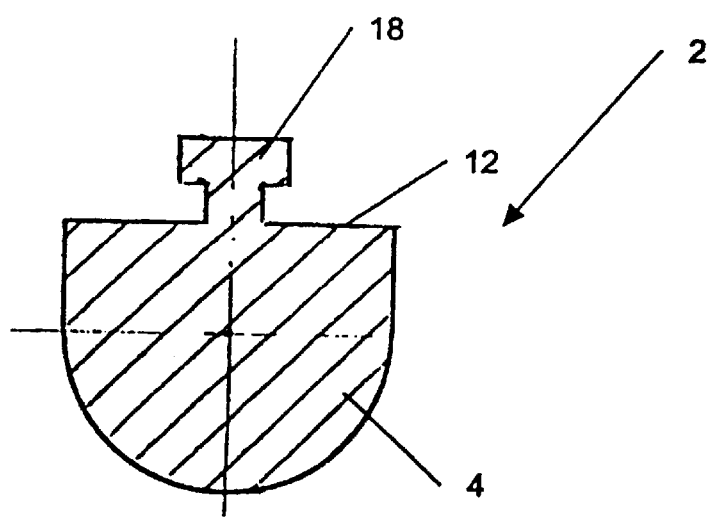
Figure 4:
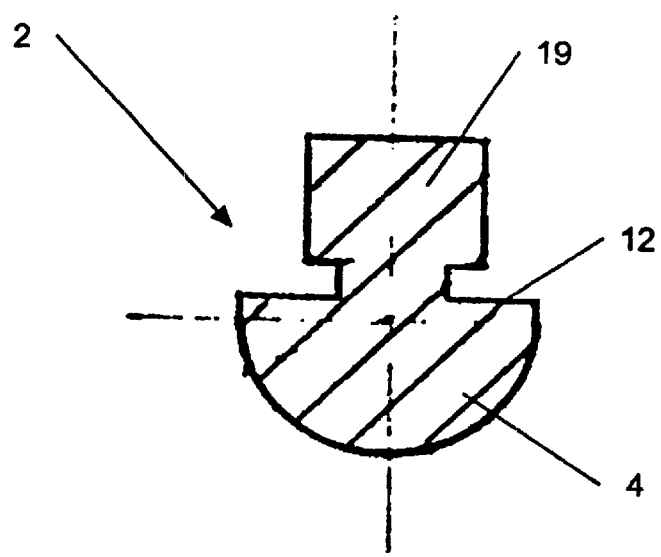

Likewise, the fixed clamping jaw 4 comprises, in the vicinity of the tip 15, another T-shaped peg 19 which improves the guiding of the mobile clamping jaw 8 over the entirety of its travel (FIGS. 3, 4).

Moreover, the T-shaped peg 19 possesses, towards the peg 18, a portion 19a of a lesser height than that envisaged for the peg 19.

FIGS. 7 to 14 show the element, or mobile clamping jaw 8, which comprises, at one of its ends and within its thickness, an arcuate recess 20. Through this recess passes a drive spindle 21 which interacts with the mobile grip 5 to convert the rotary movements of the said grip into linear movement in order for the mobile clamping jaw 8 to slide on the fixed clamping jaw 4.

Figure 8:
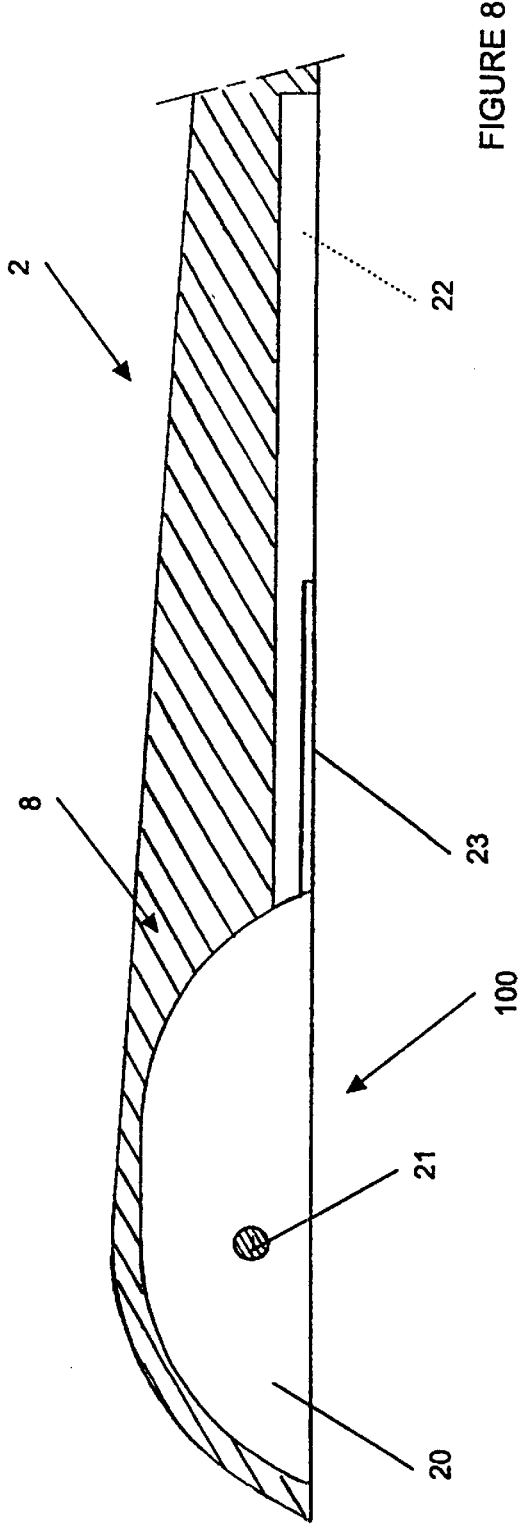
Figure 9:
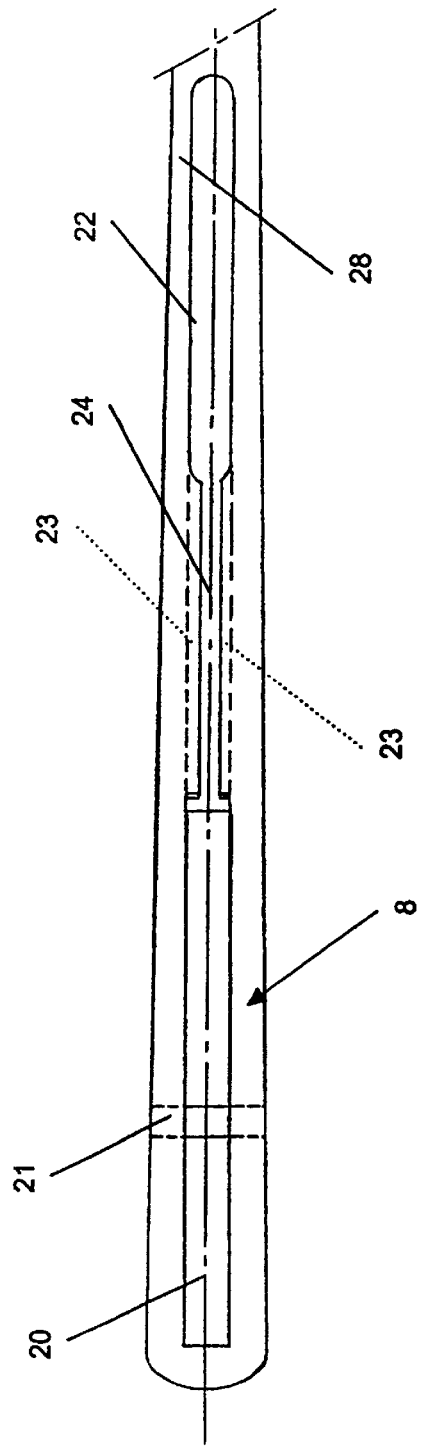

The recess 20 communicates with a groove 22 which extends towards the other end of the mobile clamping jaw 8. The groove 22 possesses, immediately in the extension of the recess 20, opposite ribs 23 separated by an aperture 24 to form a slide which interacts with the T-shaped peg 18 of the fixed clamping jaw 4 (FIGS. 8, 9).

The opposite ribs 23 extend into a portion of the groove 22 to form a zone within which the peg 18 is not guided, to permit, in accordance with a defined angular position, the positioning or withdrawal of the mobile clamping jaw 8.

Figure 11:
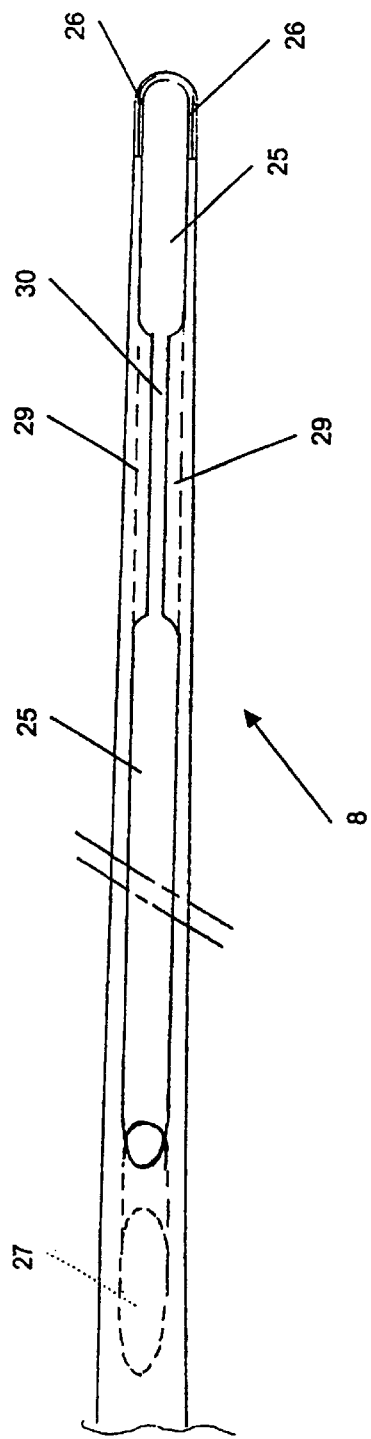
Figure 10:
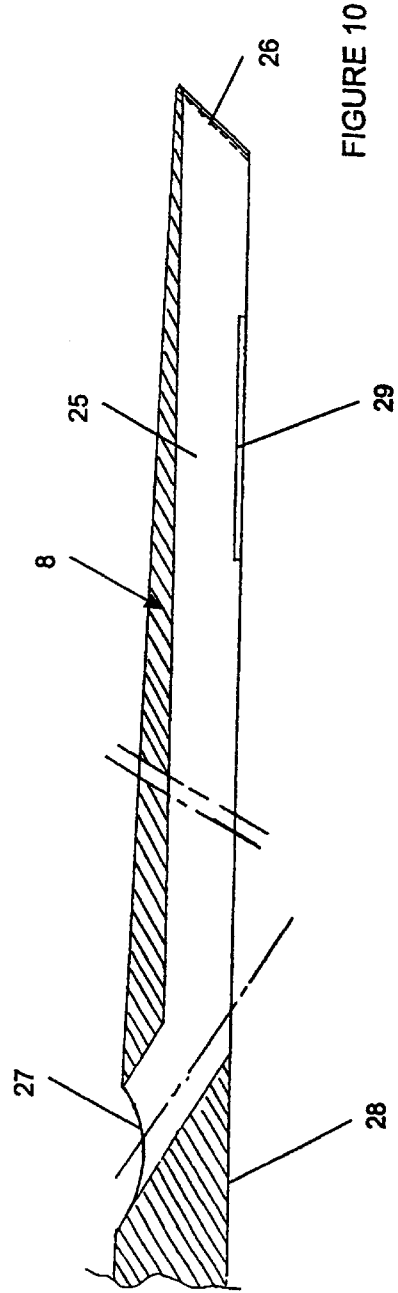

The latter comprises in its inner portion a channel 25 opening opposite to the recess 20 at the position of an inclined end formed by inclined edges 26 which are machined to possess a cutting profile (FIGS. 10, 11).

Figure 13:
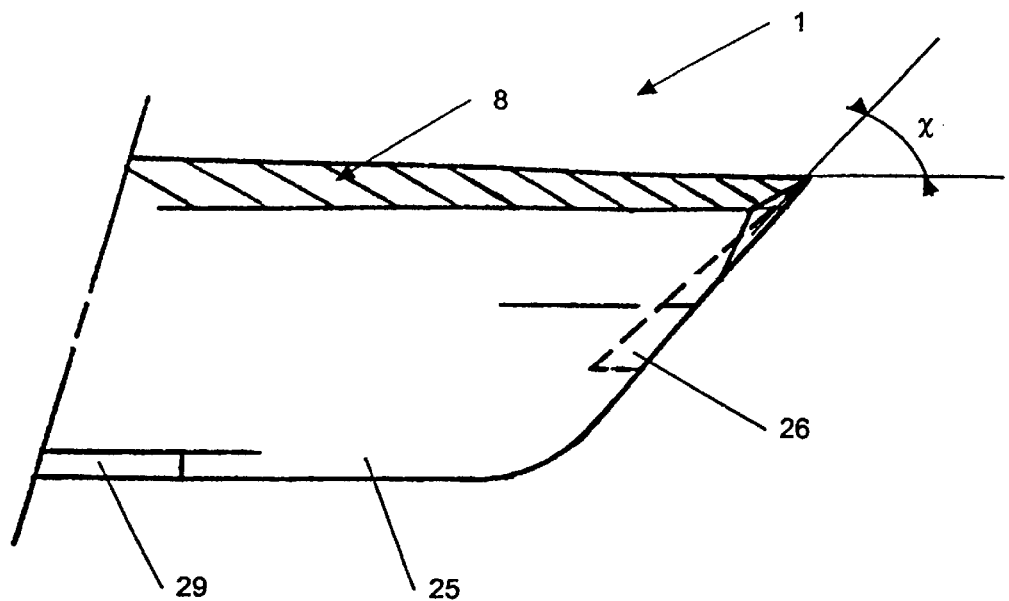
Figure 14:
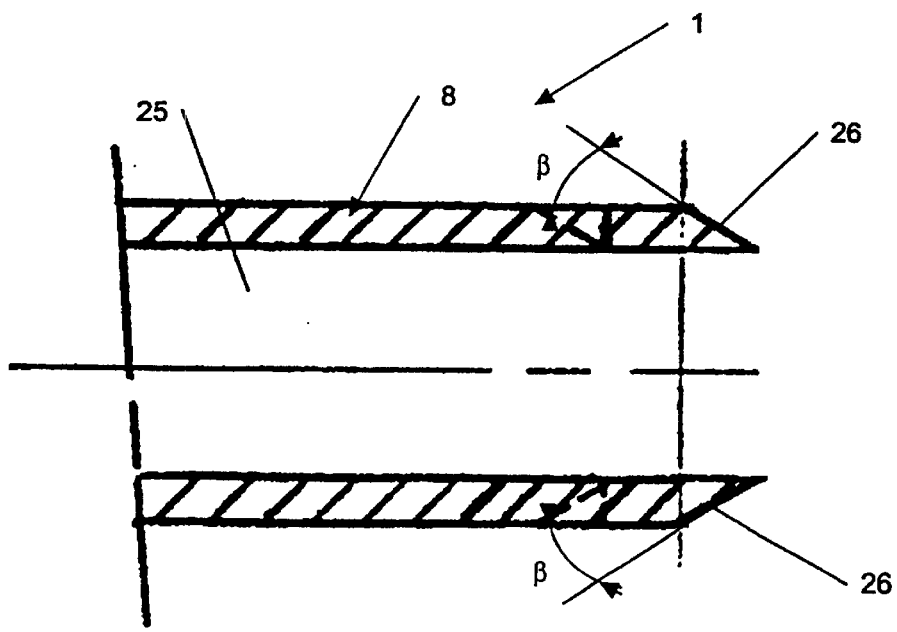

The opposite edges 26 of the inclined end of the mobile clamping jaw 8 are chamfered outwards at an angle $\beta$ of approximately 30 degrees relative to the outer edge of the said clamping jaw (FIGS. 13, 14).

Furthermore, the upper portions of the opposite edges 26 of the mobile clamping jaw 8 are chamfered towards the interior of the channel 25 at an angle $\chi$ of approximately 30 degrees relative to the upper edge of the said clamping jaw.

The channel 25 extends towards the recess 20 to open outwards and into the upper portion of the mobile clamping jaw 8 via an oblong opening 27.

It will be noted that the channel 25 is designed to form a magazine making it possible to retain the bone fragments cut away by means of the chamfered edges 17 and 26 of each clamping jaw, both fixed 4 and mobile 8.

The channel 25 possesses, in the vicinity of the inclined edges 26 and at the position of the lower edge 28 of the mobile clamping jaw 8, opposite ribs 29 separated by an aperture 30 so as to constitute a slide which interacts with the T-shaped peg 19 of the fixed clamping jaw 4 (FIG. 11).

It will be noted that the channel 25 of the mobile clamping jaw 8 possesses a U-shaped profile which is open towards the lower edge 28.

Figure 15:
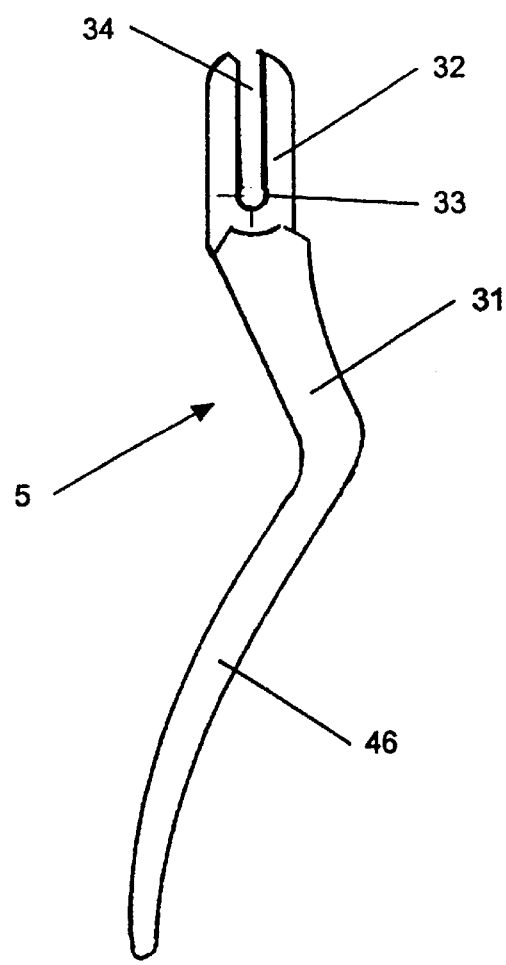
FIG. 15 is a view showing the mobile grip of the surgical instrument.
Figure 16:
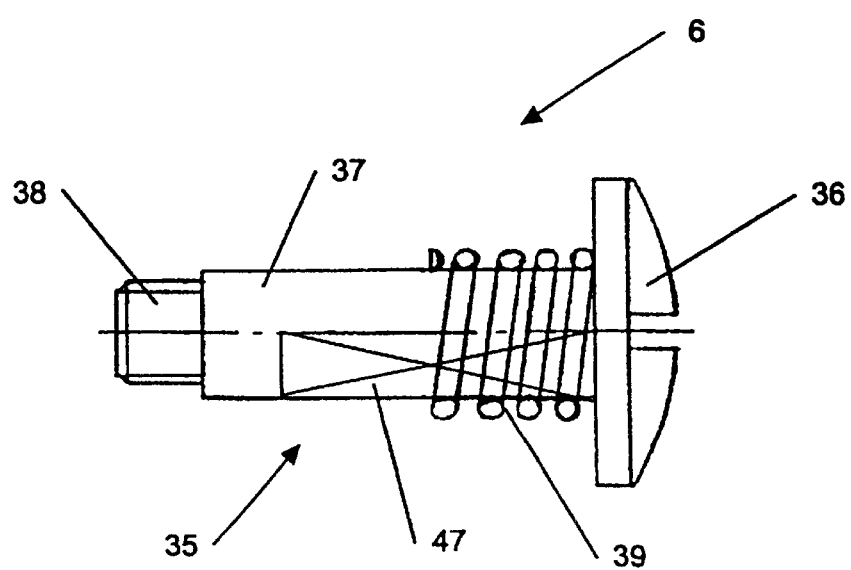
FIGS. 16 to 18 are views showing the pivot of the mobile grip on the main body of the surgical instrument.
Figure 18:
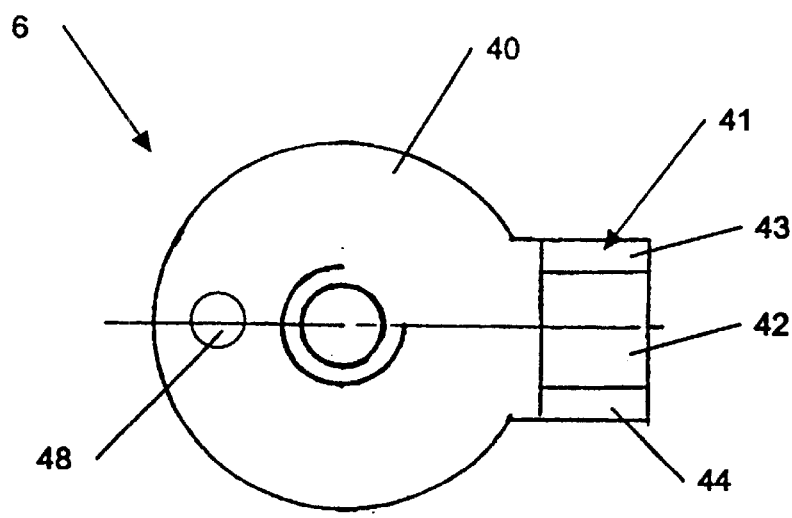
Figure 17:
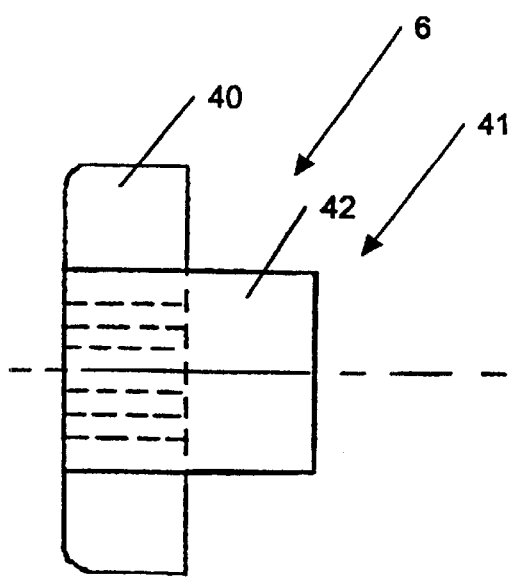

FIG. 15 shows in detail the mobile grip 5, which possesses an angled section formed by a short first branch 31 extended by a longer second branch 46.

The first branch 31 is extended, opposite to the second branch 46, by a plate 32 pierced by a drilled hole 33 communicating with an oblong and open-ended aperture 34.

The drilled hole 33 is designed with a diameter slightly greater than that envisaged for the oblong aperture 34.

The drilled hole 33 is designed to accommodate the pivot 6 in order that the grip 5 may pivot about the latter when it is mounted on the main body 2 of the instrument 1.

The oblong aperture 34 made in the plate 32 of the grip 5 is designed to receive the drive pin 21 passing through the recess 20 of the mobile clamping jaw 8.

FIGS. 16 to 20 show in detail the various elements forming the pivot 6 allowing the pivoting of the mobile grip 5 relative to the main body 2.

The pivot 6 is formed by a screw 35 having a tightening head 36 solidly fixed to a cylindrical body 37 whose end opposite the said head possesses a threaded portion 38.

A compression spring 39 is arranged around the cylindrical body 37 so as to bear against the tightening head 36 and the main body 2 of the surgical instrument 1, in the assembled position.

The cylindrical body of the screw 35 possesses a diameter slightly smaller than that envisaged for the drilled hole 33, but greater than that of the oblong aperture 34.

The cylindrical body 37 possesses, on each side of its longitudinal axis and from the head 36 towards the threaded portion 38, a flattened portion 47 reducing in diameter or width over a part of its length.

The latter, contained between the diametrically opposed flattened portions 47, is of a slightly smaller size than the oblong aperture 34 of the plate 32.

The pivot 6 comprises a tightening nut 40 which interacts with the threaded portion 38 of the screw 35.

The tightening nut 40 possesses, on its periphery, an indexing finger 41 which extends towards the head 36 of the screw 35 when the said nut is screwed onto the said screw. The indexing finger 41 is disposed in a plane parallel to that containing the pivot 6 of the mobile grip 5.

The indexing finger 41 comprises an elongate portion 42 possessing two straight and parallel opposite faces 43, 44.

Figure 20:
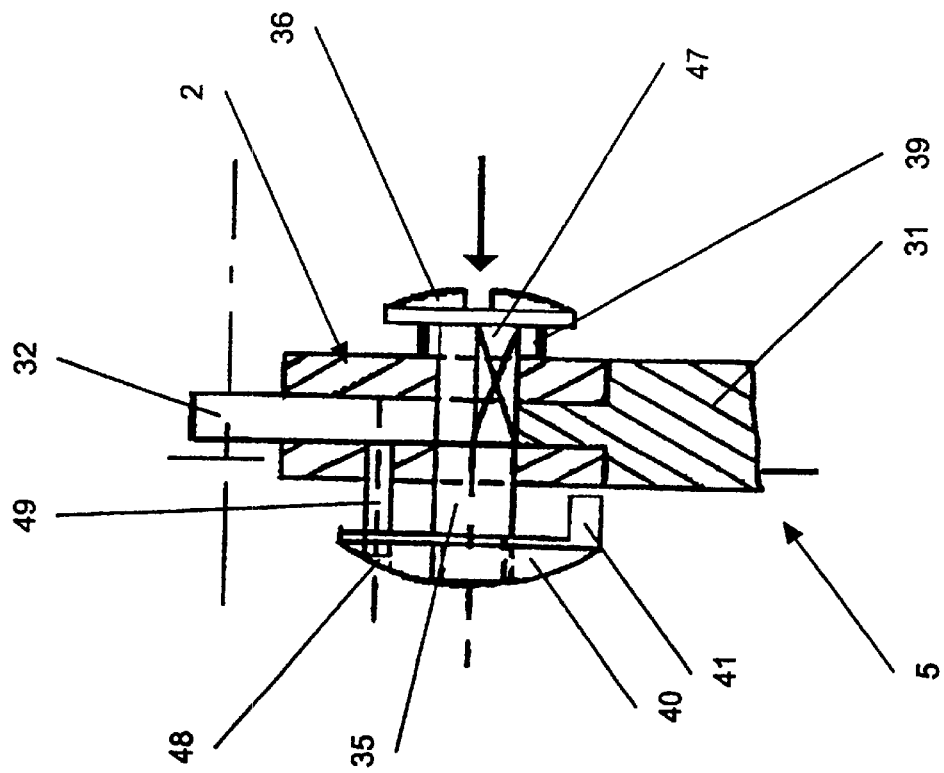
FIG. 20 is a view showing the position of the pivot for the positioning or withdrawal either of the mobile grip or of the mobile cutting element.
Figure 19:
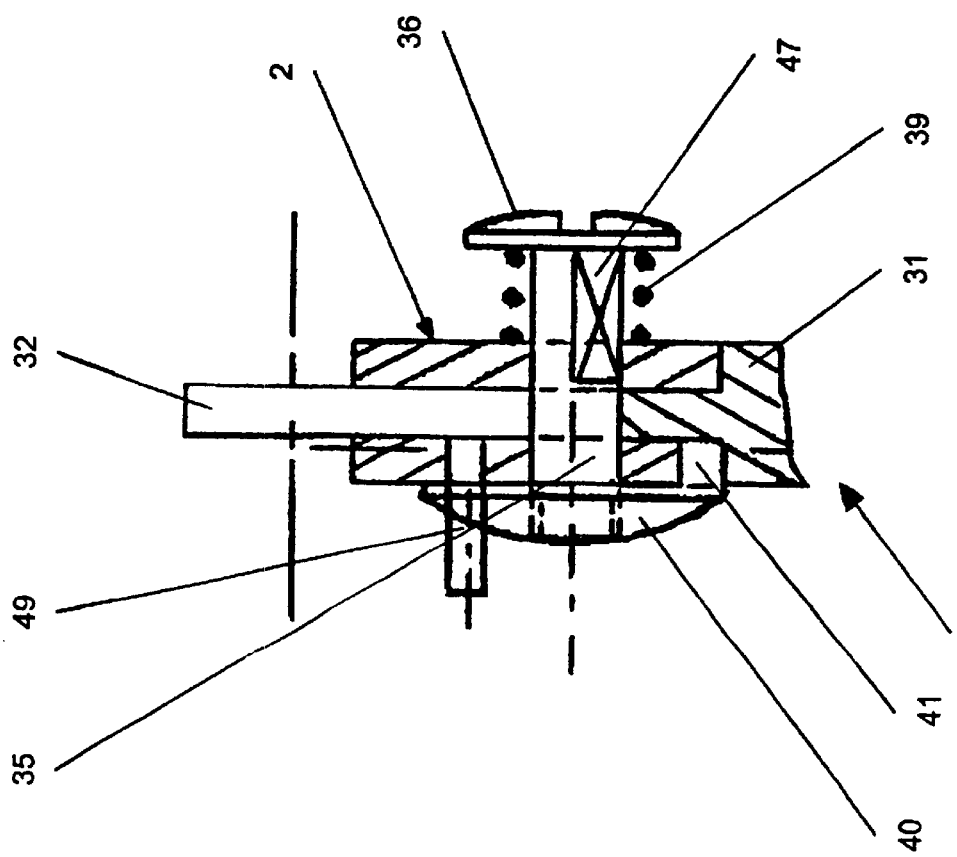
FIG. 19 is a view showing the position of the pivot when the surgical instrument is in operation.

Opposite the indexing finger 41, the tightening nut 40 comprises an open-ended hole 48 which interacts with a finger 49, extending parallel to the axis of the drilled holes 14 and solidly fixed to the main body 2 for the translatory guidance of the pivot 6 (FIGS. 19 and 20).

The assembly of the instrument 1 comprises screwing the pivot 6 onto the main body 2 in a manner such that its tightening screw 35 provided with the spring 39 is introduced into the drilled hole 14 of the first lug 13 and then passes through the other drilled hole 14 of the second lug 13 to allow the nut 40 to be screwed onto the threaded portion 38 of the cylindrical body 37.

The assembly of the mobile grip 5 between the two lugs 13 of the main body 2 takes place when the spring 39 of the pivot 6 is compressed to present the flattened portions 47 within the aperture 9 (FIG. 20).

Figure 21E:
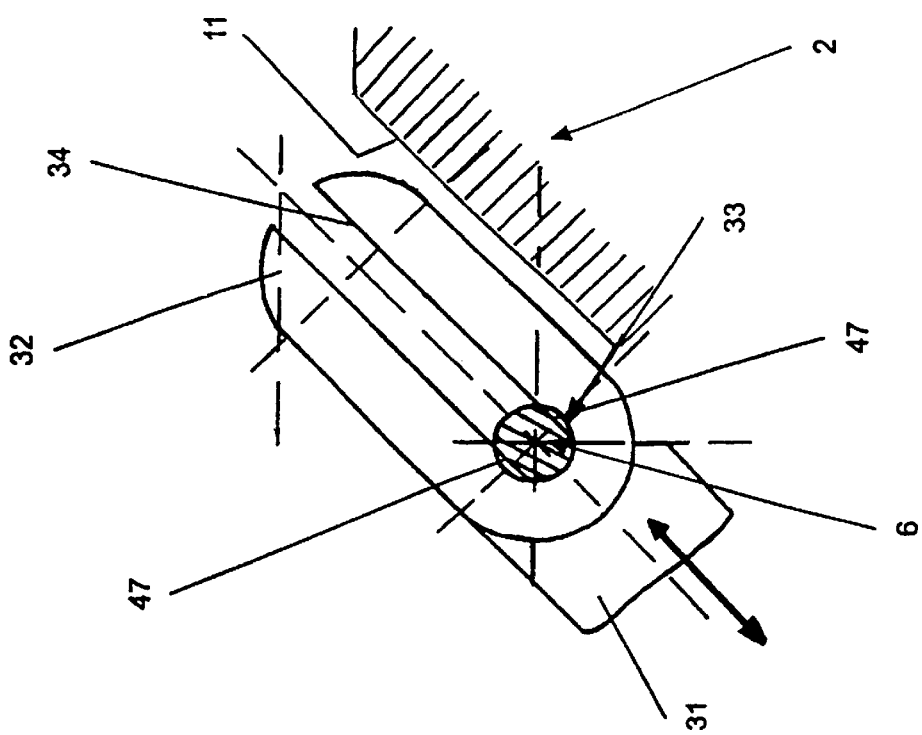

Specifically, in this position, the nut 40 is moved away from the main body allowing the plate 32 of the grip 5 to be presented in an inclined position and bearing against the surface 11 of the aperture 9 (FIGS. 21e; 22e).

It will be noted that the flattened portions 47 f the pivot 6 interact with the aperture 34 of the late 32 until the said pivot is accommodated in the drilled hole 33.

Locking of the grip 5 on the main body 2 is achieved when the pressure on the pivot 6 is withdrawn.

The transverse movement of the pivot 6 under the force of the spring 39 enables the flattened portions 47 of the screw 35 to be positioned outside the drilled hole 33 to prevent any communication with the aperture 34, as a result of the difference in diameter between the latter and the screw 35 (FIG. 19).

The positioning of the grip 5 on the main body 2 enables the plate 32 to pass through the aperture 9 and to emerge above the upper edge 12 of the fixed clamping jaw 4 in order to present the oblong aperture 34 for the assembly of the mobile element 8.

Figure 21A:
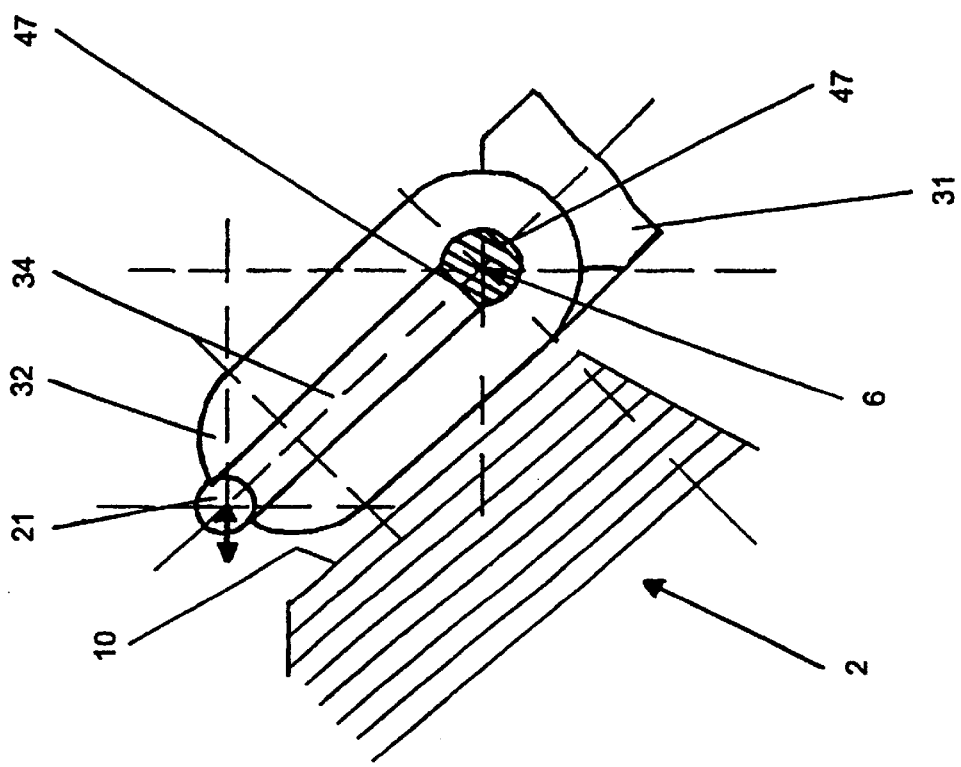
Figures 22B, 22C, 22D:
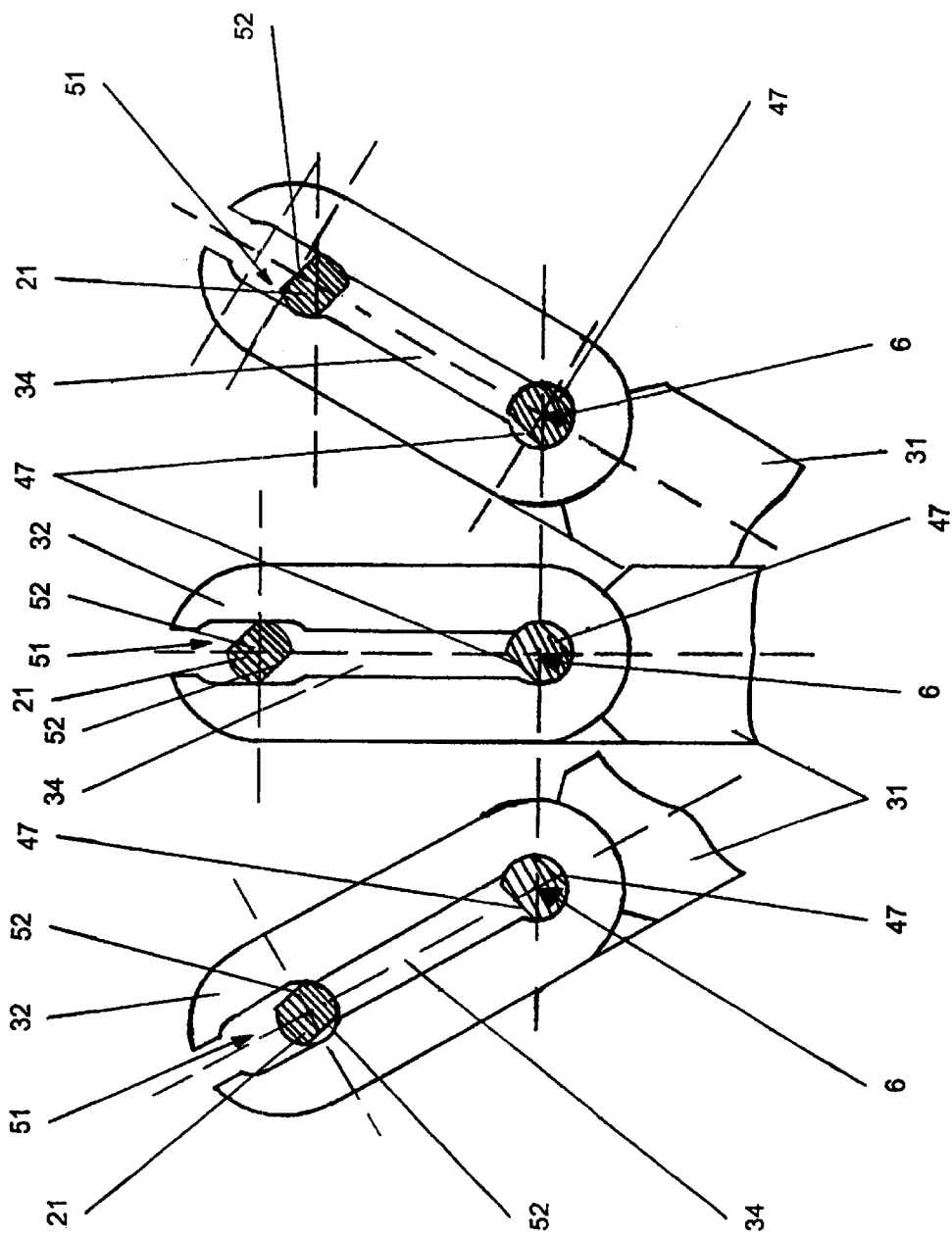

The positioning of the mobile clamping jaw 8 on the fixed clamping jaw 4 can only be achieved when the plate 32 of the mobile grip 5 is in the immediate vicinity of the inclined surface 10 of the aperture 9 of the main body 2 (FIGS. 21a, 22a).

For this purpose, it is therefore necessary to exert further pressure to the head 36 of the screw 35 of the pivot 6 in order to compress the spring 39 and release the elongate portion 42 of the indexing finger 41 of the nut 40 (FIG. 20).

As soon as the portion 42 is withdrawn from its original position, the mobile grip 5, under the force of the elastic means 7, can pivot through a few additional degrees about its pivot 6 in order for the indexing finger 41 to bear against the branch 31 and the shoulder SO.

In this position, the plate 32 of the grip 5 is placed in the immediate vicinity of the inclined surface 10 in order for the aperture 34 to be directed towards the rear of the main body 2 so as to free its access. The position of the plate 32 allows the introduction of the drive spindle 21 passing through the recess 20 of the mobile clamping jaw 8 in the oblong aperture 34.

It will be found that, in this position, the flattened portions 47 of the pivot 6 are not disposed parallel to the edges of the aperture 34, thus preventing any possibility of withdrawal of the mobile grip 5.

Simultaneously with the positioning of the spindle 21 in the aperture 34, the T-shaped peg 18 of the fixed clamping jaw 4 is accommodated in the groove portion 22 furthest from the recess 20 of the mobile clamping jaw 8, while the peg 19 interacts with the channel 25 provided towards the inclined end of the said mobile clamping jaw.

It is then sufficient to press lightly on the mobile grip 5, compressing the elastic restoring means 7, for it to pivot about the pivot 6, thus permitting the indexing finger 41 to be restored to its original position under the action of the spring 39.

Figures 21B, 21C, 21D:
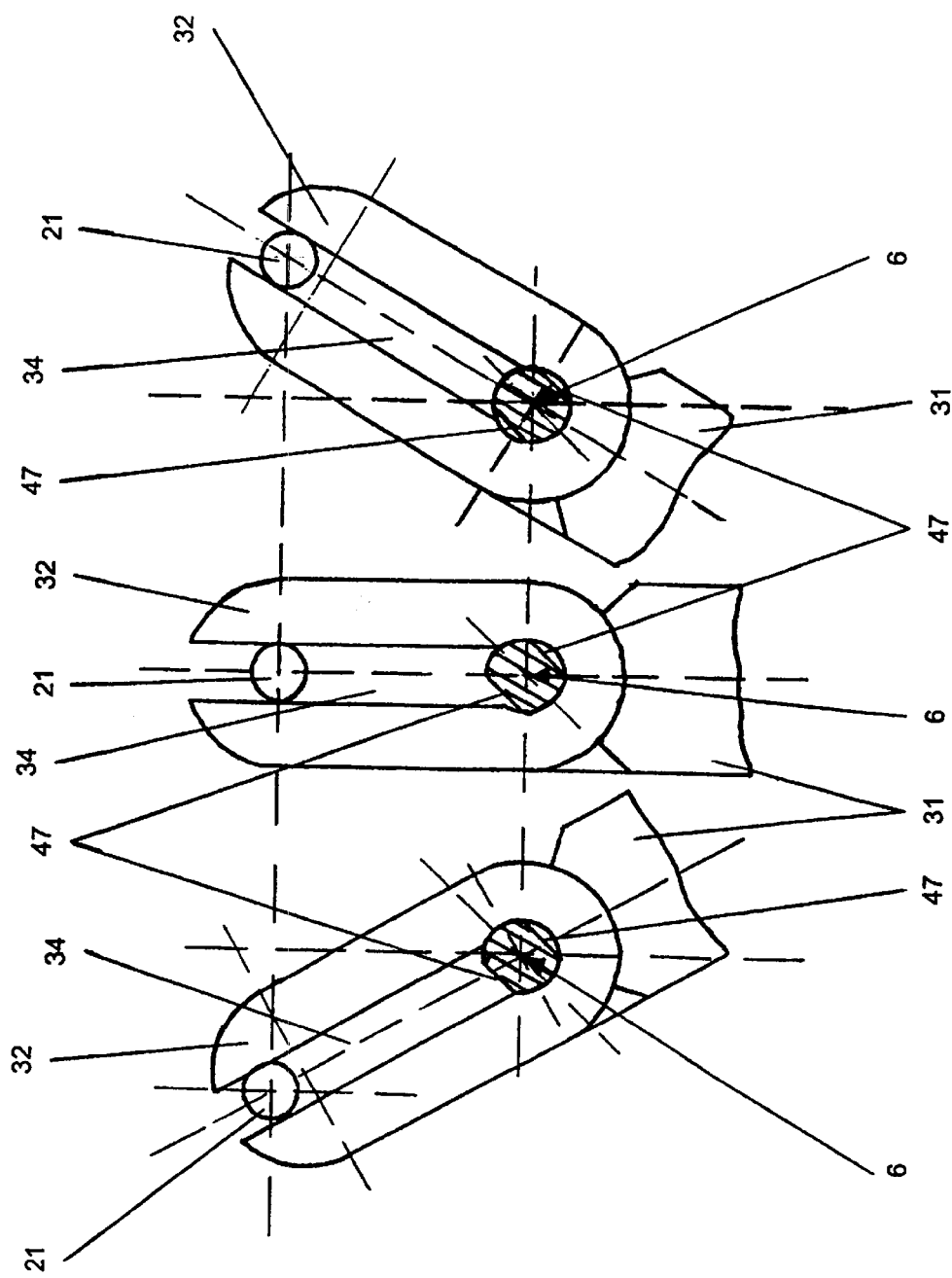
FIGS. 21b to 21d and 22b to 22d are views illustrating the positions of the mobile grip and of the pin of the mobile cutting element in operation when the pivot is in the position according to FIG. 19.

In operation, the mobile grip 5, solidly fixed to the plate 32, allows the displacement of the mobile clamping jaw 8 on the fixed clamping jaw 4 between an open position, where the chamfered edges 17 and 26 are moved apart from one another, and a closed position, where the chamfered edges 17 and 26 bear against one another (FIGS. 21b, 21c, 21d; 22b, 22c, 22d).

Specifically, the angular range of movement of the mobile grip 5 within the aperture 9 of the main body 2 is limited by the indexing finger 41 of the pivot 6 to allow the translatory movement of the mobile clamping jaw 8 on the fixed clamping jaw 4 in accordance with defined longitudinal movements.

It will be noted that the grip 5 is automatically restored to its position of rest, in other words when the clamping jaws 4 and 8 are opened by the agency of the elastic restoring means 7 provided between the said mobile grip 5 and the fixed grip 3 of the main body 2.

The transition from the open position to the closed position of the clamping jaws 4 and 8 enables the surgeon to cut fragments of bone or soft tissue by means of the chamfered edges 17, 26.

The pieces cut away during the successive movements of the mobile clamping jaw 8 on the fixed jaw 4 are recovered in the channel 25 to prevent their falling amid the operating area.

The profile of the peg 19, possessing a portion 19a of lesser height, makes it possible to prevent the build-up within the channel 25 of pieces of tissue cut away by the chamfered edges 17, 26.

When the channel 25 is filled with fragments of bone or soft tissue, it is possible to extract them through the oblong opening 26 made in the upper part of the mobile clamping jaw 8.

The connecting device 100 allows the mobile clamping jaw 8 to be withdrawn from the main body 2, independently of the mobile grip 5, for the recovery of the fragments of bone or soft tissue, following a procedure reversing that described above for its positioning.

Specifically, it is sufficient to apply pressure to the head 36 of the screw 35 of the pivot 6 in order to compress the spring 39 and release the elongate portion 42 of the indexing finger 41 of the nut 40 from its original position between the branch 31 and the shoulder 50 (FIG. 20).

As soon as the portion 42 is withdrawn from its original position, the mobile grip 5, under the force of the elastic means 7, can pivot through a few additional degrees about its pivot 6 in order for the indexing finger 41 to bear against the branch 31 and the shoulder 50.

In this position, the plate 32 of the grip 5 is placed in the immediate vicinity of the inclined surface 10 in order for the aperture 34 to be directed towards the rear of the main body 2 so as to free its access.

The position of the plate 32 allows the withdrawal of the spindle 21 from the oblong aperture 34, and the simultaneous release of the ribs 23 and 29 from the plugs 18 and 19 for withdrawal of the mobile clamping jaw 8 of the main body 2 (FIGS. 21a, 22a).

The mobile grip 5 may likewise be dismantled when it is necessary to carry out complete sterilization of the surgical instrument 1.

For this purpose, it is necessary to unlock the elastic means 7 in order to release the mobile grip 5 from the fixed grip 3 of the main body 2.

Subsequently, it is sufficient to exert pressure on the head 36 of the screw 35 of the pivot 6 in order to compress the spring 39 and release the elongate portion 42 of the indexing finger 41 of the nut 40 from its original position between the branch 31 and the shoulder 50 (FIG. 20).

In this position, the plate 32 of the mobile grip 5 is positioned in the immediate vicinity of the inclined surface 11 of the aperture 9, while the flattened portions 47 of the screw 35 are disposed parallel to the edges of the oblong aperture 34 in order for the pivot 6 to be able to slide within the latter for the purpose of withdrawal of the grip 5 (FIGS. 21e, 22e).

FIGS. 22a to 22e show an alternative embodiment of the profile of the oblong aperture 34 of the plate 32 when the surgical instrument 1 possesses no peg 18 on the main element 2 for the guiding of the mobile element 8.

It will be noted that the oblong aperture 34 possesses, opposite the drilled hole 33, and in accordance with its longitudinal axis, an oblong seating 51 which possesses a greater width than that envisaged for the said aperture.

Likewise, the drive spindle 21 disposed inside the recess 20 of the mobile element possesses diametrically opposed flattened portions 52 which define a spindle size which is substantially smaller than the width of the oblong aperture 34.

By contrast, the diameter of the drive spindle 21 is greater than the width of the aperture 34 to prevent its extraction in the operating position of the surgical instrument, as explained previously (FIGS. 22b to 22d).

The positioning or withdrawal of the mobile element 8 takes place in the same manner as described above, specifically in that the plate 32 must again be in the vicinity of the inclined surface 10 to allow the introduction of the drive spindle 21 in order that its flattened portions 52 are disposed parallel to the opposite edges of the oblong seating 51.

In the operating position, it will be found that the drive spindle 21 retained in the seating 52 constitutes a means for guiding the mobile element 8, preventing its withdrawal under the compressive forces necessary to cut away fragments of bone or soft tissue between the inclined and chamfered edges 17, 26.

It will be noted that the connecting device 100 according to the present invention may be provided on other surgical instruments to permit, in a given position, the positioning or the withdrawal of the mobile element 8 and of the mobile grip 5 of the said instrument.

What is claimed is:

1. A connecting device for a surgical instrument, comprising at least one mobile cutting element which is mounted to move reciprocally along a fixed jaw of the surgical instrument under action of a resiliently loaded mobile grip, and an indexing means for operatively connecting the mobile cutting element to the mobile grip, the indexing means being movable to a first angular position permitting mounting or removal of the mobile element relative to the fixed jaw, and a second angular position spaced from the first, for the mounting or removal of the mobile grip relative to the fixed jaw.

2. The connecting device according to claim 1, wherein the indexing means includes:
   a resiliently loaded pivot for pivotally connecting the mobile grip relative to a fixed grip of a main body of the surgical instrument, and
   guide means fixed to the mobile grip and interacting with the pivot and a drive spindle fixed on the mobile cutting element and engageable by the mobile grip to move the mobile cutting element relative to the main body.

3. The connecting device according to claim 2, wherein said pivot includes a screw, a spring and a nut fixed to an indexing finger provided with an elongate portion to limit rotational movement of the mobile grip.

4. The connecting device according to claim 3, wherein said screw is formed by a cylindrical body portion, a tightening head, and a threaded portion for receiving the nut, and the body portion having diametrically opposed flattened portions which reduce a diameter of the body portion of the screw.

5. The connecting device according to claim 3, wherein the nut includes opposite the indexing finger, an open-ended hole designed to receive a guide finger fixed to the main body of the surgical instrument.

6. The connecting device according to claim 2, wherein the mobile grip includes an inner plate having an opening therein which communicates with an oblong aperture which receives the drive spindle of the mobile cutting element, and the pivot extending through the opening.

7. The connecting device according to claim 6, wherein the oblong aperture has a width substantially greater than a width defined between opposed flattened portions of the pivot to permit, in the second angular position, either the mounting or the removal of the mobile grip.

8. The connecting device according to claim 6, wherein the oblong aperture opposite the opening, has an oblong seat for receiving the drive spindle, and the drive spindle is provided with flattened portions for guidance of the mobile cutting element.

9. The connecting device according to claim 8, wherein a distance separating the flattened portions of the drive spindle is less than the width of the oblong aperture to permit, in the first angular position, either the mounting or the removal of the mobile cutting element.

10. The connecting device according to claim 2, wherein the main body includes an aperture having inclined surfaces which respectively define extreme angular positions of movement of the mobile grip.

11. A surgical instrument comprising at least one mobile cutting element which is mounted to move reciprocally along a fixed jaw of the surgical instrument under action of a resiliently loaded mobile grip, and an indexing means for operatively connecting the mobile cutting element to the mobile grip, the indexing means being moveable to a first angular position permitting mounting or removal of the mobile cutting element, and a second angular position, spaced from the first, for the mounting or removal of the mobile grip.

12. The surgical instrument according to claim 11, wherein the indexing means includes:
   a resiliently loaded pivot for pivotally connecting the mobile grip relative to the fixed grip of a main body of the surgical instrument, and
   guide means fixed to the mobile grip and interacting with the pivot, and a drive spindle fixed on the mobile cutting element and engageable by the mobile grip to move the mobile cutting element relative to the main body.

13. The surgical instrument according to claim 12, wherein the pivot includes a screw and a nut fixed to an indexing finger provided with an elongate portion to limit rotational movement of the mobile grip.

14. The surgical instrument according to claim 13, wherein the screw has a cylindrical body portion, a head, and a threaded portion for receiving the nut, and said body portion having portion diametrically opposed flattened portions reducing a diameter of the body portion of the screw.

15. The surgical instrument according to claim 13, wherein the nut includes, opposite the indexing finger, an open-ended hole designed to receive a guide finger fixed to the main body of the surgical instrument.

16. The surgical instrument according to claim 12, wherein the mobile grip includes an inner end plate portion having an opening which communicates with an oblong aperture which receives the drive spindle of the mobile cutting element and the pivot being mounted within the opening.

17. The surgical instrument according to claim 16, wherein the oblong aperture has a width greater than a width between flattened portions of the pivot to permit, in the second angular position, either the mounting or the removal of the mobile grip.

18. The surgical instrument according to claim 16, wherein the aperture has an oblong seat spaced from the opening for receiving the drive spindle, and the spindle being provided with flattened portions for guidance of the mobile cutting element.

19. The surgical instrument according to claim 18, wherein a distance separating the flattened portions of the drive spindle is less than the width of the oblong aperture to permit, in the first angular position, either the mounting or the removal of the mobile cutting element.

20. The surgical instrument according to claim 12, wherein the main body includes an aperture having inclined surfaces which respectively define extreme angular positions of movement of the mobile grip.

* * * * *